United States Patent [19]
Davis et al.

[11] Patent Number: 6,048,065
[45] Date of Patent: Apr. 11, 2000

[54] DISTANCE OPTIMIZING APPARATUS FOR A PLACIDO-BASED EYE OBSERVATION SYSTEM

[75] Inventors: Neil M. Davis, Marcola; Vincent F. Brancaccio, Eugene, both of Oreg.; Dale A. Rorabaugh, Rancho Sante Fe, Calif.

[73] Assignee: Vismed, Incorporated, San Diego, Calif.

[21] Appl. No.: 09/154,603

[22] Filed: Sep. 16, 1998

[51] Int. Cl.[7] .................................................. A61B 3/10
[52] U.S. Cl. ............................................................ 351/221
[58] Field of Search .................................... 351/209, 210, 351/211, 212, 213, 221, 246, 247; 128/898; 606/107, 166; 623/5

[56] References Cited

U.S. PATENT DOCUMENTS

| | | |
|---|---|---|
| 4,189,215 | 2/1980 | Humphrey . |
| 4,252,420 | 2/1981 | Kohayakawa . |
| 4,370,033 | 1/1983 | Kani et al. . |
| 4,452,235 | 6/1984 | Reynolds .................................. 128/898 |
| 4,795,250 | 1/1989 | Nakamura et al. . |
| 4,834,527 | 5/1989 | Kobayashi . |
| 4,881,807 | 11/1989 | Luce et al. . |
| 4,999,009 | 3/1991 | Matsumura . |
| 5,110,200 | 5/1992 | Snook ..................................... 351/212 |
| 5,473,392 | 12/1995 | Klopotek . |
| 5,521,657 | 5/1996 | Klopotek . |
| 5,548,354 | 8/1996 | Kasahara et al. . |
| 5,585,872 | 12/1996 | Kohayakawa . |
| 5,841,511 | 11/1998 | D'Souza et al. ......................... 351/212 |

FOREIGN PATENT DOCUMENTS

PCT/US95/13993  5/1996  WIPO .

*Primary Examiner*—George Manuel
*Attorney, Agent, or Firm*—Fleshner & Kim, LLP

[57] ABSTRACT

An apparatus assists a user of a placido-based eye observation system to place the placido at an optimum distance from an observed eye. A light source is configured as a point source. The light source and a CCD camera are attached to the placido at opposed locations that are spaced from the viewing axis, but symmetric with respect to it. Light is emitted by the source towards the eye, and reflected by the apex of the cornea of the eye on the main axis. The reflected source light appears in the field of view of the CCD camera as a bright point image. The location of the point image within the field of view informs how far away the eye is from the placido. The placido is moved until the point image is positioned within the field of view at a reference position. In a manual embodiment a screen shows what is in the field of view, and an operator looks at the screen and uses a joystick to control movement of the placido. In an automated embodiment a computer analyzes the field of view, determines the position of the point image, and drives a closed loop system to maintain the distance at the optimum value.

26 Claims, 3 Drawing Sheets

DISTANCE OPTIMIZING APPARATUS FOR A PLACIDO-BASED EYE OBSERVATION SYSTEM

BACKGROUND OF THE INVENTION

1. Field of the Invention

The present invention relates to the field of eye observation systems used in the ophthalmic fields of corneal topography, ophthalmometry, keratometry and tonometry, and particularly to apparatus used in placido-based eye observation systems for positioning the placido at the optimum distance from the eye along a viewing axis.

2. Description of Related Art

Eye observation systems sometimes feature placidos, also known as placido members, for projecting a special light pattern onto the eye that is observed. The eye is observed along a viewing axis through a hole in the center of the placido member. The light pattern is projected from a special placido surface in the front side of the member. The placido surface is typically either flat or three dimensional, e.g. a cone. The surface consists of a series of concentric rings of alternating dark and bright colors. The bright rings, which are also known as mires, are typically translucent and illuminated from the rear. The surface thus projects images of the mires onto the eye. The mire pattern is reflected on the cornea of the eye, and is thus observed together with the eye.

The eye observation system is typically designed to observe the eye when the cornea is at an optimum distance from the placido surface. While that distance is fixed, the mechanism needed to achieve it must be adjustable, as individual faces vary. This is a well known problem in the prior art. Additional information is found in U.S. Pat. No. 4,881,807 to Luce et al., and in PCT Application No. PCT/US95/13993 published May 9, 1996 as publication No. WO 96/13199, the contents of which documents are incorporated herein by reference.

SUMMARY OF THE INVENTION

The present invention provides an apparatus for assisting a user of a placido-based eye observation system to place the placido at the optimum distance from the eye.

The apparatus of the invention includes a light source configured as a point source and a light detector. Both are positioned relative to the placido at locations that are off the viewing axis, but symmetric with respect to it. Light is emitted by the source towards the eye, reflected by the apex of the cornea of the eye on the main axis, and received by the detector. The reflected source appears to the detector as a bright point image. The perceived location of the point image is dependent upon how far away the eye is from the placido.

It is preferred that the light detector is a CCD camera with a field of view. It is known that, when the distance is optimized, the point image is aligned with a corresponding position, such as the center, in the field of view. To optimize the distance, the placido is moved until the point image has been centered in the field of view.

In a preferred embodiment the light source emits infrared light. An IR pass filter in front of the detector eliminates everything from the field of view except the point image. In a manual embodiment a screen shows what is in the field of view. An operator uses a joystick or other control to move the placido until the distance has been optimized. In an automated embodiment a computer analyzes the field of view, determines the position of the point image, and drives a closed loop system to maintain the distance at the optimum value.

The present invention thus provides a system for optimizing the observation distance which is independent of the optical system used for on-axis viewing. The resulting system has few components and yet provides for very accurate positioning of a cornea along the viewing axis. These and other features and advantages of the present invention will be apparent from the preferred embodiment described in the following detailed description and illustrated in the accompanying drawings.

DETAILED DESCRIPTION OF THE PREFERRED EMBODIMENT(S)

Figure 1:
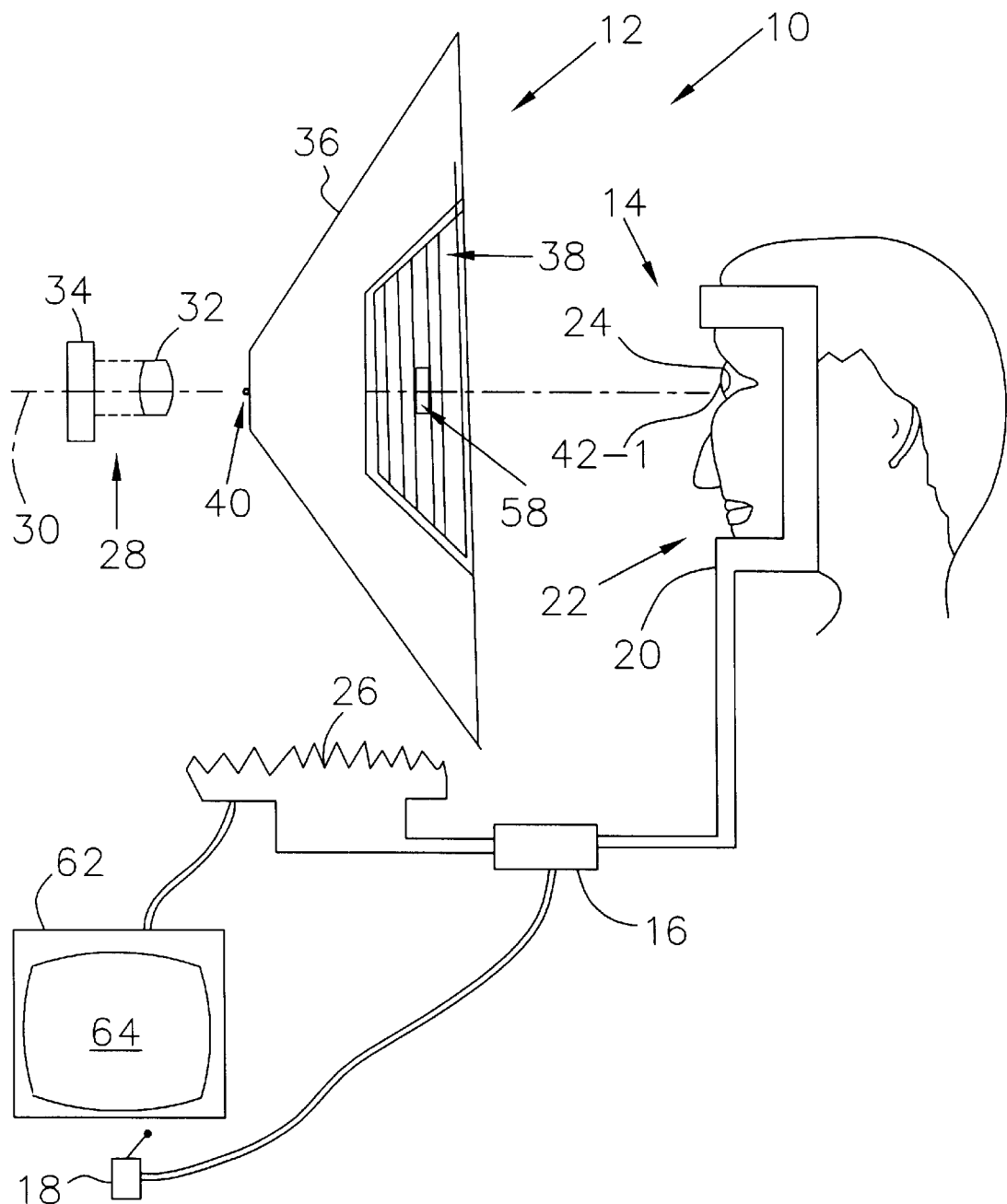
FIG. 1 is a side view of salient components of a placido featuring eye observation system that includes the apparatus of the invention.

As has been mentioned, the invention provides an apparatus for positioning the placido of an eye observation system at the optimum distance from the observed eye. Such an eye observation system is described initially with reference to FIG. 1.

Placido featuring eye observation system 10 includes an imaging assembly 12 and a patient station 14, that are movable with respect to each other. The movement is made via a control means 16 such as a stepper motor. The control means also includes an input means 18 that receives commands suitable for controlling the movement. The input means can be automatic or manual, such as a joystick 18.

Patient station 14 includes a frame 20 that receives and supports a patient's face 22, and helps the patient keep the eye being observed steady in front of the imaging assembly. Device 20 usually includes a chin rest and forehead stop.

The salient components of imaging assembly 12 are optical, and are shown dissociated from their physical support 26 for clarity. Imaging assembly 12 includes a main camera 28 that has a viewing axis 30. Camera 28 is preferably implemented with a lens 32 and a CCD array 34.

The imaging assembly also includes a placido cone 36, a portion of which is shown cut out and enlarged for clarity. The placido cone has a placido surface 38 that defines a center 40. The surface is typically centered around viewing axis 30. The surface receives independent illumination from a light source in the rear (not shown). The patient's eye 24 generally looks along axis 30, and is imaged by main camera 28.

Figure 2:
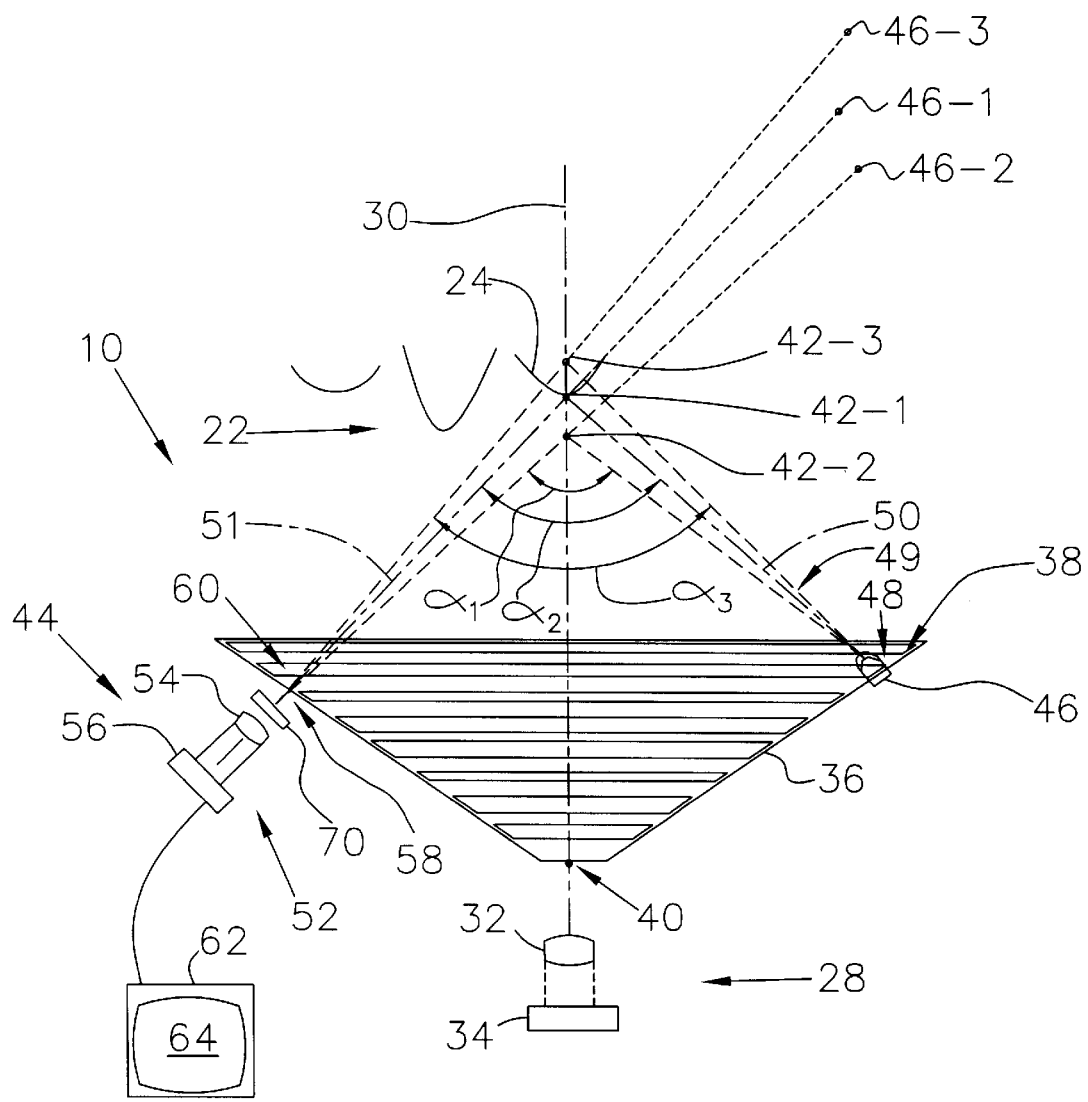
FIG. 2 is a plan view of the preferred embodiment of a distance optimizing apparatus made according to the invention.

The distance to be optimized, also known as the observation distance, is a distance from eye 24 to center 40 of the placido surface. As also seen in FIG. 2, the distance is optimized when eye 24 is exactly at a target point 42-1 on the viewing axis 30. The control means is thus used first to align eye 24 with viewing axis 30. Then the control means is used to adjust the observation distance, while maintaining the alignment.

The apparatus of the invention is now described with reference to FIG. 2. Apparatus 44 includes a light source 46 that is also known as light source means. In its simplest embodiment, the light source is an infrared (IR) LED that is attached onto a source portion 48 of surface 38. Alternately, the light source can be behind surface 38, and emitting light through a source opening in the surface at the source portion. It is preferred that the source portion is within a black ring of the placido surface.

The light source emits a bundle 49 of light rays generally aimed toward target point 42-1. The light source is preferably a point source, which permits the beam to be considered diverging, and thus increases resolution. When eye 24 is in the vicinity of the target point, the light rays are incident upon the cornea and are reflected accordingly.

Apparatus 44 also includes what is also known as light detection means 52. The preferred light detection means is referred to herein as a depth camera 52. Camera 52 is situated such that it receives at least one reflected light ray. As such, the depth camera also receives an image of the entire eye and immediately surrounding area.

It is preferred that light source 46 and depth camera 52 are located at an equal distance from center 40, and at diametrically opposing points. This ensures that the light ray that is received by the depth camera is one that has been reflected off of the apex of the cornea, when the eye is centered on axis 30. In that case, the ray is considered to have been emitted in a first or incident propagation direction, and to have been reflected by the eye in a second or reflected propagation direction.

When the eye is exactly at target point 42.1 the first propagation direction is denoted by numeral 50 in FIG. 2, and the second propagation direction is denoted by numeral 51. Propagation directions 50 and 51 define an angle $\alpha_1$ between them. Preferably angle $\alpha$ equals 90° for the accuracy of the apparatus to be optimized. Other values will also produce acceptable results, with the preferred range being within 15° of 90°.

The depth camera may be implemented by a lens 54 and a CCD array 56. It is preferred that the depth camera is behind surface 38, and receiving light through a detection opening 58 in the surface 38. The detection opening is at a portion 60 of placido surface 38 that is otherwise known as the detection portion. It is preferred that the detection portion is within a black ring in the placido surface.

An important aspect of the invention is that the light source and the light detection means are fixed with respect to the placido surface. Moreover, as will be apparent from the description below, the field of view of the depth camera is at a fixed orientation with respect to the surface.

The first and second propagation directions thus intersect the placido surface at source portion 48 and detection portion 60 respectively. It is also preferred that the source and detection portions are located such that each of the first and second propagation directions defines equal angles equal to $\alpha/2$ from viewing axis 30. It is further preferred that the placido surface, which is typically circularly symmetric, is centered around viewing axis 30, in which case the source portion and the detection portion are equidistant from center 40.

It should also be noted that light source 46, target point 42-1 and depth camera 52 are shown generally disposed in a horizontal plane that also includes viewing axis 30. Although such is the preferred embodiment, it is not necessary that they be disposed in a horizontal plane.

In a manual embodiment of the invention, the apparatus informs the operator how far the observation distance is from being optimized. The apparatus includes a monitor 62 with a screen 64. The screen is coupled with CCD array 56 and displays the images received by the CCD array. These images are now described with reference to FIGS. 3–8. All these images appear bounded by field of view 68 of CCD array 56.

Figure 3:
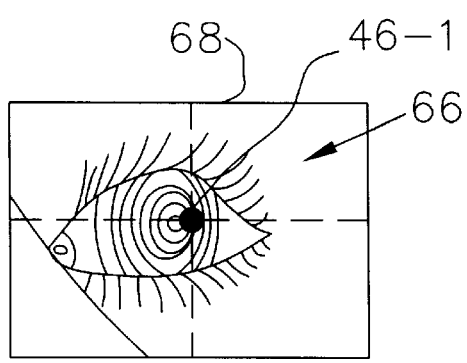
FIGS. 3, 5 and 7 illustrate views of an eye, as sensed by what is referred to as a depth camera of the invention.

FIG. 3 shows an image 66, also known as the first Perkinge image, received by CCD array 56 when eye 24 is exactly at target point 42-1. The image includes the eye, the reflected mire pattern, and the reflection of light source 46, which appears as a bright point image 46-1. The vertical and horizontal dashed lines have been added in FIG. 3 to more clearly identify the position of the point image.

The important information is the position of the point image with respect to the field of view, which is also called position information. The position information is derived from the orientation of the second propagation direction relative to a frame of reference that is fixed with respect to the placido surface. This is accomplished by securing the detector in a fixed spatial relationship with respect to the placido member. If the detector is a CCD array, the frame of reference is its field of view.

Figure 4:
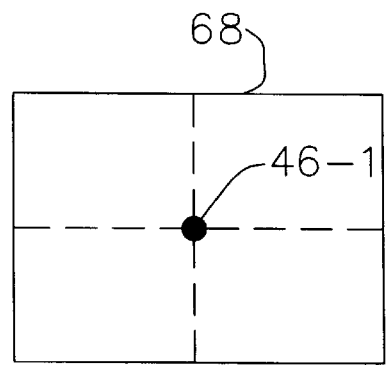
FIGS. 4, 6 and 8 illustrate the views of FIGS. 3, 5 and 7 respectively, wherein additionally an image minimizing filter has been placed in front of the depth camera.

Preferably light source 46 emits IR light, and an IR pass filter 70 is positioned in front of CCD array 56. Filter 70 thus filters out the visible light image, which includes the eye and the mire pattern. This leaves only point image 46-1 as a bright spot in an otherwise dark background, as is illustrated in FIG. 4. The filter thus minimizes the image down to a point, which is easier to identify.

When the observation distance is exactly optimized, the position of the point image with respect to the field of view is recorded as a reference position for the apparatus. It is also preferred but not necessary that the depth camera is initially oriented so that the reference position is at the exact center of the field of view, as shown in FIGS. 3 & 4.

Figure 5:
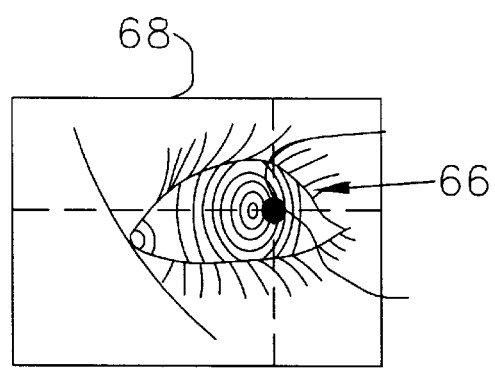
Figure 6:
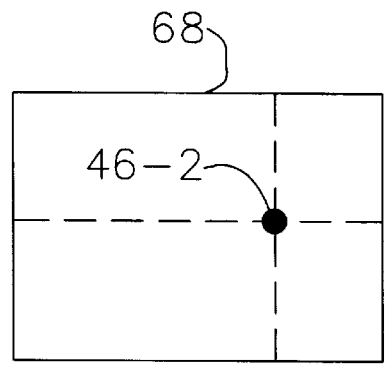
Figure 7:
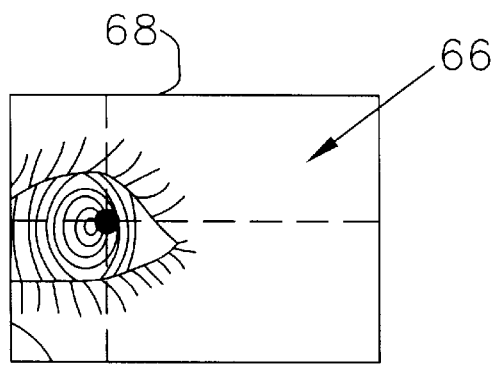
Figure 8:
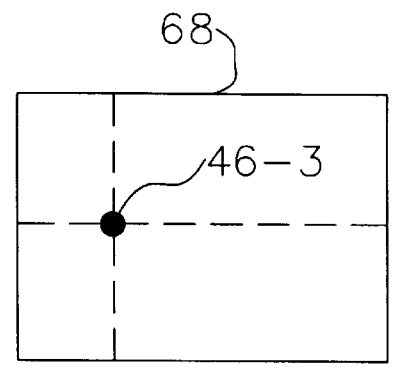

Returning to FIG. 2, eye 24 can be in the position represented by point 42-2, which is too close to main camera 28 on the viewing axis. The angle between the first and second propagation direction, defined by the light rays, is shown as $\alpha_2$ which is greater than angle $\alpha_1$. FIG. 5 shows the Perkinge image, which is positioned more to the right side than it was in FIG. 3. If filter 70 is used, the image of FIG. 5 is reduced to point image 46-2 of FIG. 6, which again is positioned more to the right side than the reference position of FIG. 4.

It is also possible that the eye is too far away from the main camera, such as at point 42-3, shown in FIG. 2. Then the light rays form an angle $\alpha_3$ that is smaller than angle $\alpha_1$. When this is the case, the depth camera receives images such as those shown in FIGS. 7 and 8. As is seen, image 66 and point image 46-3 are to the left of the center of the field of view. This relationship can also be visualized in FIG. 2, where point images 46-1, 46-2, 46-3 have been plotted at their apparent positions with respect to the field of view of depth camera 52.

It is seen that the axial position of the eye is indicated by the horizontal position of the reflected light source with respect to the field of view. Indeed, the operator looking at the screen sees images such as those in FIGS. 3, 5 or 7, or as those in FIGS. 4, 6, or 8 if a filter is used. Then, if necessary, he uses the joystick to adjust the observation distance until the point image is shifted to the reference position of FIG. 3 or 4 respectively, while keeping the eye centered on axis 30. When that happens, it will be known that the apex of the cornea of the eye has been positioned at target point 42-1.

In an alternate, automated embodiment, the apparatus of the invention includes a computer programmed for controlling the control means continuously. The computer examines the digitized, frame-grabbed CCD video image, identifies the horizontal position, and measures its separation from the reference position. The input means of the control means includes a closed loop feedback system that receives the measured separation as error information. The apparatus then maintains the distance at the optimum value continuously.

It will be appreciated that the depth camera senses movement along a horizontal axis. Other devices which provide sensing along a line could also be used to perform this function. For instance a linear photodiode or photoreceptor array would also work. It would also be possible to use a linear or two-dimensional position-sensitive photodetector. In a photodetector embodiment, the reflected light could be defocused so that it is large enough to strike two photodiodes. If the spot between two photodiodes corresponds to the desired position of the cornea, then the cornea is moved along the viewing axis until the signals from the two adjacent photodiodes are equal. These embodiments would be lighter and less expensive than a CCD camera.

Although the present invention has been described in detail with reference to a particular preferred embodiment, persons possessing ordinary skill in the art to which this invention pertains will appreciate that various modifications and enhancements may be made without departing from the spirit and scope of the claims as written and as judicially construed according to principles of law. The above disclosure is thus intended for purposes of illustration and not limitation.

The invention claimed is:

1. An apparatus for monitoring an observation distance between an eye and a placido member of a system for observing an eye, comprising:
    a light source that emits a beam of electromagnetic radiation towards the eye; and
    a detector configured to receive electromagnetic radiation from the emitted beam that is reflected by the eye, wherein
    the detector generates position information indicative of the observation distance, and
    the light source and the detector are arranged on opposite sides of a viewing axis between the eye and a center of the placido member.

2. The apparatus of claim 1, wherein the light source and the detector are attached to the system for observing the eye, and the light source and the detector are spaced approximately equally from the center of the placido member.

3. The apparatus of claim 1, wherein the light source is attached to a surface of a placido member.

4. The apparatus of claim 3, wherein the placido member has a design that includes dark colored rings, and wherein the light source is attached onto a dark colored ring.

5. The apparatus of claim 1, wherein a source opening is formed in a surface of a placido member, and wherein the light source emits the beam through the source opening.

6. The apparatus of claim 5, wherein the placido member has a design that includes dark colored rings, and wherein the source opening is within a dark colored ring.

7. The apparatus of claim 1, wherein a detection opening is formed in a surface of a placido member, and wherein the reflected electromagnetic radiation is received through the detection opening.

8. The apparatus of claim 7, wherein the placido member has a design that includes dark colored rings, and wherein the detection opening is within a dark colored ring.

9. The apparatus of claim 7, wherein the detector is a CCD array.

10. The apparatus of claim 7, wherein the detector is a linear photodiode.

11. The apparatus of claim 7, wherein the detector is a photoreceptor array.

12. The apparatus of claim 1, wherein the light source emits infrared light, and wherein the detector comprises an IR pass filter.

13. The apparatus of claim 1, further comprising a display screen coupled with the detector and configured to display the position information.

14. The apparatus of claim 1, wherein an angle between propagation directions of the emitted and reflected electromagnetic radiation is approximately $90°±15°$ when the observation distance equals the optimum.

15. The apparatus of claim 1, wherein the light source emits the beam of electromagnetic radiation toward a cornea of the eye, and the detector is configured to receive electromagnetic radiation from the emitted beam that is reflected by the cornea of the eye.

16. The apparatus of claim 15, wherein the light source emits the beam of electromagnetic radiation towards an apex of the cornea, and the detector is configured to receive the electromagnetic radiation from the emitted beam that is reflected by the apex of the cornea.

17. A system for observing an eye of a patient, comprising:
    a placido member having a placido surface that is centered around a viewing axis;
    a patient station opposite the placido member, the patient station admitting the patient's face and supporting it in such a way that the patient's eye that is to be observed looks towards the placido surface;
    a control device, responsive to position commands, configured to cause relative movement between the placido member and the patient station;
    a light source configured to emit a beam of electromagnetic radiation towards the patient's eye when the patient's head is supported in the patient station; and
    a detector configured to receive a portion of the emitted electromagnetic radiation that is reflected from the patient's eye, wherein
    the detector is also configured to generate position information indicative of an observation distance between the patient's eye and the placido member, and the light source and the detector are arranged on opposite sides of the viewing axis of the placido member.

18. The observation system of claim 17, wherein the light source emits infrared light, and wherein the detector comprises an IR pass filter.

19. The observation system of claim 17, wherein the control device is configured to maintain an optimum observation distance based on the position information generated by the detector.

20. The apparatus of claim 19, wherein an angle between propagation directions of the emitted and reflected electromagnetic radiation is approximately $90°±15°$ when the observation distance equals the optimum.

21. The observation system of claim 19, further comprising a display screen, coupled to the detector, for displaying the position information.

22. The observation system of claim 19, further comprising a processor configured to monitor the position information and to generate the position commands used by the control device based on the position information.

23. The observation system of claim 17, further comprising a user input device that generates the position commands used by the control device.

24. The apparatus of claim 17, wherein the light source and the detector are attached to the system for observing the eye, the light source and the detector are spaced approximately equally from a center of the placido member.

25. The apparatus of claim 17, wherein the light source is configured to emit a beam of electromagnetic radiation towards a cornea of the patient's eye, and the detector is configured to receive a portion of the emitted electromagnetic radiation that is reflected from the cornea of the patient's eye.

26. The apparatus of claim 25, wherein the light source is configured to emit a beam of electromagnetic radiation towards an apex of the cornea, and the detector is configured to receive the portion of the emitted electromagnetic radiation that is reflected from an apex of the cornea.

* * * * *